(12) United States Patent
Silverman et al.

(10) Patent No.: US 6,248,058 B1
(45) Date of Patent: Jun. 19, 2001

(54) METHOD FOR TREATING TRACHEO-ESOPHAGEAL FISTULAS

(75) Inventors: David E. Silverman, Palo Alto; Alan Stein, Moss Beach, both of CA (US)

(73) Assignee: Enteric Medical Technologies, Inc., Foster City, CA (US)

( * ) Notice: Subject to any disclaimer, the term of this patent is extended or adjusted under 35 U.S.C. 154(b) by 0 days.

(21) Appl. No.: 09/286,531

(22) Filed: Apr. 5, 1999

Related U.S. Application Data

(63) Continuation-in-part of application No. 09/232,056, filed on Jan. 15, 1999.
(60) Provisional application No. 60/111,884, filed on Dec. 11, 1998.

(51) Int. Cl.[7] .................................................... A61F 2/00
(52) U.S. Cl. ......................................................... 600/29
(58) Field of Search ............................... 600/29; 606/198

(56) References Cited

U.S. PATENT DOCUMENTS

| | | | |
|---|---|---|---|
| 3,094,122 | 6/1963 | Gauthier et al. | 128/221 |
| 3,204,634 | 9/1965 | Koehn | 128/214 |
| 4,271,827 | 6/1981 | Angelchik | 128/1 R |

(List continued on next page.)

FOREIGN PATENT DOCUMENTS

| | | | |
|---|---|---|---|
| AU-A-34223/95 | 5/1996 | (AU) | A61K/9/10 |
| WO 97/19643 | 6/1997 | (WO) | A61B/17/12 |
| WO 97/45131 | 12/1997 | (WO) | A61K/33/04 |
| WO 98/01088 | 1/1998 | (WO) | A61F/2/08 |
| WO 98/17200 | 4/1998 | (WO) | A61F/2/02 |
| WO 98/17201 | 4/1998 | (WO) | A61F/2/02 |

OTHER PUBLICATIONS

Donahue, P. et al., "Endoscopic Sclerosis Of The Gastric Cardia For Prevention Of Experimental Gastroesophageal Reflux" (1990) *Gastrointestinal Endoscopy*, pp. 253–258.

Society of Am. Gastrointestinal Endoscopic Surgeons, Los Angeles, CA, "Granting of Privileges for Laparascopic General Surgery", (Mar. 1991), *Am. Jrnl. of Surgery*, vol. 161, pp. 324–325.

Aye, R.W. et al., "Early Results With the Laparoscopic Hill Repair", (May 1994), *Am. Jrnl. of Surgery*, vol. 167, pp. 542–546.

Collard, J.M. et al., "Laparoscopic Antireflux Surgery/What is Real Progress?", (1994), *Annals of Surgery*, vol. 220, No. 2, pp. 146–154.

DeMeester, T.R. et al., "Nissen Fundoplication for Gastroesophageal Reflux Disease", (1986), *Annals of Surgery*, vol. 204, No. 1, pp. 9–20.

Donahue, P.E. et al., "The Floppy Nissen Fundoplication/Effective Long–term Control of Pathologic Reflux", (Jun. 1985), *Arch Surg*, vol. 120, pp. 663–668.

Ellis, Jr., F.H., "The Nissen Fundoplication", (1992), *Ann. Thorac. Surg.*, vol. 54, pp. 1231–1235.

Grande, L. et al., "Value of Nissen Fundoplication in patients with gastro–oesophageal reflux judged by long–term sympton control", (1994), *Brit. Jnl. of Surgery*, vol. 81, pp. 548–550.

(List continued on next page.)

*Primary Examiner*—Cary O'Connor
*Assistant Examiner*—Brian Szmal
(74) *Attorney, Agent, or Firm*—Flehr Hohbach Test Albritton & Herbert LLP

(57) ABSTRACT

A method for treating a tracheo-esophageal fistula. The method comprises the steps of augmenting the wall forming the esophagus in the vicinity of the fistula and placing a stent over the fistula in the esophagus so as to inhibit material traveling down the esophagus from passing into the trachea. The augmenting of the wall facilitates support of the stent in the esophagus so as to enhance isolation of the fistula.

20 Claims, 5 Drawing Sheets

U.S. PATENT DOCUMENTS

| | | | |
|---|---|---|---|
| 4,351,333 | 9/1982 | Lazarus et al. | 128/214.4 |
| 4,424,208 | 1/1984 | Wallace et al. | 424/177 |
| 4,582,640 | 4/1986 | Smestad et al. | 260/123.7 |
| 4,773,393 | 9/1988 | Haber et al. | 600/30 |
| 4,803,075 | 2/1989 | Wallace et al. | 424/423 |
| 4,837,285 | 6/1989 | Berg et al. | 530/356 |
| 5,007,940 | 4/1991 | Berg | 623/66 |
| 5,067,965 | 11/1991 | Ersek et al. | 623/66 |
| 5,116,387 | 5/1992 | Berg | 623/66 |
| 5,158,573 | 10/1992 | Berg | 623/66 |
| 5,204,382 | 4/1993 | Wallace et al. | 523/115 |
| 5,258,028 | 11/1993 | Ersek et al. | 623/11 |
| 5,301,682 | 4/1994 | Debbas | 128/737 |
| 5,314,473 | 5/1994 | Godin | 623/12 |
| 5,336,263 | 8/1994 | Ersek et al. | 623/11 |
| 5,451,406 | 9/1995 | Lawin et al. | 424/423 |
| 5,480,644 | 1/1996 | Freed | 424/436 |
| 5,490,984 | 2/1996 | Freed | 424/436 |
| 5,580,568 | 12/1996 | Greff et al. | 424/423 |
| 5,645,559 * | 7/1997 | Hachtman et al. | 606/198 |
| 5,667,767 | 9/1997 | Greff et al. | 424/9.411 |
| 5,695,480 | 12/1997 | Evans et al. | 604/264 |
| 5,755,658 | 5/1998 | Wallace et al. | 600/30 |
| 5,785,642 | 7/1998 | Wallace et al. | 600/30 |
| 5,792,478 | 8/1998 | Lawin et al. | 424/502 |
| 5,830,178 | 11/1998 | Jones et al. | 604/49 |
| 5,861,036 | 1/1999 | Godin | 623/12 |

OTHER PUBLICATIONS

Hill, L.D. et al., "Laparoscopic Hill Repair", (Jan. 1994), *Contemporary Surgery*, vol. 44, No. 1, pp. 13–20.

Hunter, J.G. et al., "A Physiologic Approach to Laparoscopic Fundoplication for Gastroesophageal Reflux Disease", (1996), *Annals of Surgery*, vol. 223, No. 6, pp. 673–687.

Ireland, A.C. et al., "Mechanisms underlying the antireflux action of fundoplication", (1993), *Gut*, vol. 34, pp. 303–308.

Johansson, J. et al., "Outcome 5 years after 360° fundoplication for gastro–oesophageal reflux disease", (Jan. 1993), *Brit. Jnl. of Surgery*, vol. 80, pp. 46–49.

Jones, C. et al., "Closure of a benign broncho–oesophageal fistula by endoscopic injection of bovine collagen, cyanoacrylate glue and gelfoam", (Jan. 1996), *Aus. & NZ Jrnl. of Surgery*, pp. 55–57.

Kauer, W.K.H. et al., "Mixed Reflux of Gastric and Duodenal Juices Is More Harmful to the Esophagus than Gastric Juice Alone/The Need for Surgical Therapy Re–Emphasized", (1995) *Annals of Surgery*, vol. 222, No. 4, pp. 525–533.

Klingman, R.R. et al., "The Current Management of Gastroesophageal Reflux", (1991), *Adv. Surg.*, vol. 24, pp. 259–291.

Little, A.G., "Mechanisms of Action of Antireflux Surgery: Theory and Fact", (1992), *World Jnl. of Surgery*, vol. 16, pp. 320–325.

Luostarinen, M., "Nissen Fundoplication for Reflux Esophagitis/Long–Term Clinical and Endoscopic Results in 109 of 127 Consecutive Patients", (1993), *Annals of Surgery*, vol. 217, No. 4, pp. 329–337.

Luostarinen, M. et al., "Fate of Nissen fundoplication after 20 years. A clinical, endoscopical, and functional analysis", (1993), *Gut*, vol. 34, pp. 1015–1020.

Malizia, A. et al., "Migration and Granulomatous Reaction After Periurethral injection of Polytef (Teflon)", (Jun. 1984), *JAMA*, vol. 251, No. 24, pp. 3277–3281.

Martin, C. et al., "Collis–Nissen Gastroplasty Fundoplication For Complicated Gastro–Oesophageal Reflux Disease", (1992), *Aust. N.Z. Jnl. Surg.*, vol. 62, pp. 126–129.

O'Connor, K.W. et al., "Endoscopic placement of collagen at the lower esophageal sphincter to inhibit gastroesophageal reflux: a pilot study of 10 medically intractable patients", (1988), *Gastrointestinal Endoscopy*, vol. 34, No. 2, pp. 106–112.

O'Connor, K. W. et al., "An experimental endoscopic technique for reversing gastroesophageal reflux in dogs by injecting inert material in the distal esophagus", (1984) Gatrointestinal Endoscopy, vol. 30, No. 5, pp. 275–280.

Ortiz, A. et al., "Conservative treatment versus antireflux surgery in Barrett's oesophagus: long–term results of a prospective study", (1996), *Brit. Jnl. of Surg.*, vol. 83, 274–278.

Politano, V. et al., "Periurethral Teflon Injection for Urinary Incontinence", ( Feb. 1974) *Jnl.Urology*, vol. 111, pp. 180–183.

Pope, C., "The Quality of Life Following Antireflux Surgery", (1992), *World Jnl. of Surgery*, vol. 16, pp. 355–358.

Schulman, C.C. et al., "Endoscopic injections of Teflon to treat urinary incontinence in women", (Jan. 21, 1984) *BMJ*, vol. 228, p. 192.

Shafik, A., "Intraesophageal Polytef injection for the treatment of reflux esophagitis", (1996), *Surgical Endoscopy*, pp. 329–331.

Shirazi, S.S. et al., "Long–term Follow–up for Treatment of Complicated Chronic Reflux Esophagitis", (May 1987), *Arch Surg*, vol. 122, 548–552.

Spechler, S.J. et al., "Comparison of Medical and Surgicl Therapy for Complicated Gastroesophageal Reflux Disease in Veterans", (Mar. 19, 1992), *NE Jnl. of Med*, vol. 326, No. 12, pp. 786–792.

Spechler, S.J. et al., "The Columnar–Lined Esophagus, Intestinal Metaplasia, and Norman Barrett", (1996), *Gastroenterology*, vol. 110, pp. 614–621.

Thor, K.B. et al., "A Long–Term Randomized Prospective Trial of the Nissen Procedure Versus a Modified Toupet Technique", (Dec. 1989), *Ann. Surg.*, vol. 210, No. 6, pp. 719–724.

Vaezi, M.F. et al., "Synergism of acid and duodenogastroesophageal reflux in complicated Barrett's esophagus", (1995), *Surgery*, vol. 117, pp. 699–704.

Walker, R.D. et al., "Injectable Bioglass as a Potential Substitute for Injectable Polytetrafluoroethylene", (Aug. 1992), *J. Urol.*, vol. 148, pp. 645–647.

Waring, J.P. et al., "The Preoperative Evaluation of Patients Considered for Laparoscopic Antireflux Surgery", (1995), *Am. Jnl. Of Gastroenterology*, vol. 90, No. 1, pp. 35–38.

Y. Izzidian Al–Samarrai, Aal et al., "Endoscopic Obliteration of a Recurrent Tracheosophageal Fistula", (Nov. 1987), Jnl. of Pediatric Surgery, vol. 22, No. 11, p. 893.

* cited by examiner

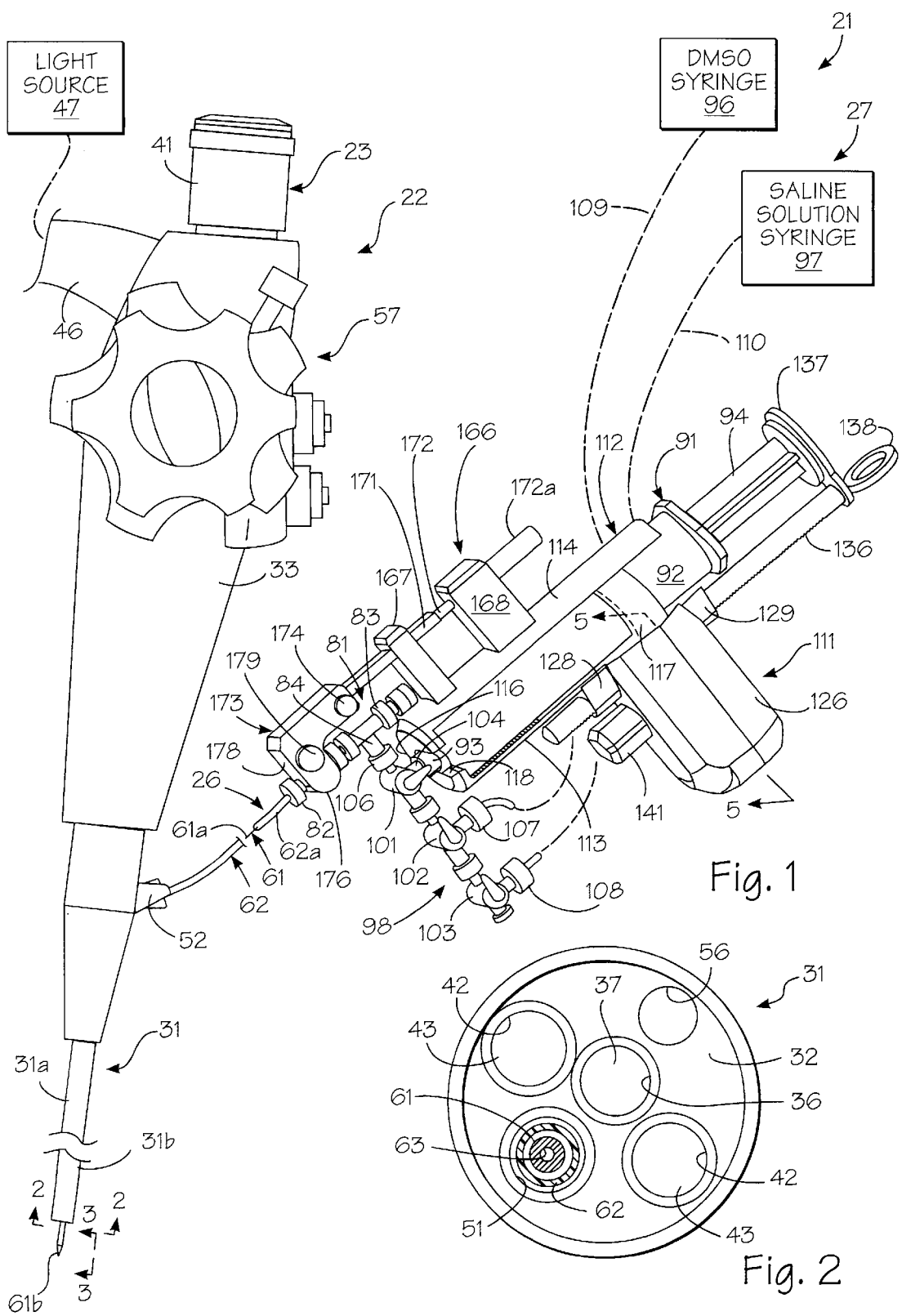

METHOD FOR TREATING TRACHEO-ESOPHAGEAL FISTULAS

This application is a continuation-in-part of U.S. patent application Ser. No. 09/232,056 filed Jan. 15, 1999 and claims priority to U.S. provisional patent application Serial No. 60/111,884 filed Dec. 11, 1998, the entire contents of each of which are incorporated herein by this reference.

This invention pertains to the treatment of tracheo-esophageal fistulas and, more particularly, to the treatment of tracheo-esophageal fistulas by means of stenting the wall of the esophagus.

Tracheo-esophageal fistulas are a serious, end stage complication of cancers arising in the lung, tracheo-bronchial tree and the esophagus. The nature and extent of the disease almost always precludes curative therapy and, therefore, palliative measures are the goals of therapy. Unfortunately, many reported successful procedures fail to improve the patients' conditions to the point that the patient is able to be released from the hospital. The "in-hospital" mortality is often higher than the 30-day mortality.

Increases in the expertise of endoscopists and esophagoscopy have permitted esophageal endoprostheses to be utilized in the treatment of tracheo-esophageal fistulas. Such procedures include stenting or other intubation of the esophagus. Unfortunately, the funnel rim of conventional stents used in this regard is often a poor fit with gaps between the rim and the mucosa of the esophageal wall. As a result, food and saliva are often allowed to pass between the mucosa and the outer surface of the prosthesis, thereby deleating the purpose of the prosthesis. In light of the foregoing, there is a need for a new and improved procedure for treating tracheo-esophageal fistulas which overcomes the disadvantages of the currently provided procedures.

In general, it is an object of the present invention to provide a minimally invasive method for treating tracheo-esophageal fistulas.

Another object of the invention is to provide a method of the above character in which a material is injected into the wall of the esophagus to form one or more implants in the wall for facilitating support of a stent in the esophagus and formation of a seal between the esophageal wall and the stent.

Another object of the invention is to provide a method of the above character in which the injected material is a nonbiodegradable material.

Another object of the invention is to provide a method of the above character in which the material is injected as at least one solution and thereafter forms a solid.

Another object of the invention is to provide a method of the above character in which the at least one solution includes a solution from which a nonbiodegradable solid precipitates.

Another object of the invention is to provide a method of the above character in which the solution includes a biocompatible polymer and a biocompatible solvent.

Another object of the invention is to provide a method of the above character in which a first plurality of implants is formed in the wall above the fistula and a second plurality of implants is formed in the wall below the fistula.

Another object of the invention is to provide a method of the above character in which a stent is placed in the esophagus to isolate the fistula.

Additional objects and features of the invention will appear from the following description from which the preferred embodiments are set forth in detail in conjunction with the accompanying drawings.

FIG. 1 is a perspective view of an apparatus for use in the method for treating tracheo-esophageal fistulas of the present invention FIG. 2 is a cross-sectional view of a portion of the apparatus of FIG. 1 taken along the line 2—2 of FIG. 1.

Figure 3:
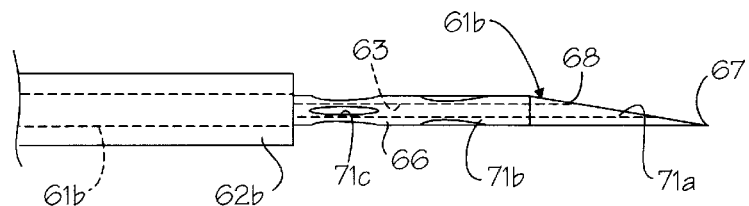
FIG. 3 is an enlarged side view of the distal portion of the apparatu of FIG. 1 taken along the line 3—3 of FIG. 1.

In general, a method for treating a tracheo-esophageal fistula is provided. The method comprises the steps of augmenting the wall forming the esophagus in the vicinity of the fistula and placing stent over the fistula in the esophagus so as to inhibit material traveling down the esophagus from passing into the trachea. The augmenting of the wall facilitates support of the stent in the esophagus so as to enhance isolation of the fistula.

The method of the present invention can be performed with an apparatus of the type shown in FIG. 1. Apparatus or medical device 21 shown therein includes a probe member or probe 22 having an optical viewing device 23. A needle assembly 26 is slidably carried by probe 22. Treatment device 21 further includes a supply assembly 27 mounted to the proximal end portion of needle assembly 26.

A conventional or other suitable gastroscope or endoscope can be used or probe 22. The exemplary probe 22 shown in FIG. 1 is an Olympus CF Type 40L/I endoscope made by Olympus Corporation of Toky Japan. Probe 22 includes a flexible elongate tubular member or insertion tube 31 having proximal and distal extremities 31a and 31b and a distal face 32. Insertion tube 31 has been sectioned 1n FIG. 1 so that only a portion of proximal extremity 31a and distal extremity 31b are shown. A handle means or assembly is coupled to proximal extremity 31a of the insertion tube 31 and includes conventional handle 33. The tubular insertion tube 31 is provided with a plurality of bores or passageways extending from proximal extremity 31a to distal extremity 31b. A plurality of five such passageways, including a central passageway 36, are shown in FIG. 2.

An optical viewing device 23 is formed integral with conventional probe 22 and has an optical element or objective lens 37 carried by the central passageway 36 of insertion tube 31. The lens 37 has a field of view at distal face 32 which permits the operator to view forwardly of insertion tube distal extremity 31b. Optical viewing device 37 further includes an eye piece 41 mounted on the proximal end of handle 33. Second and third illumination passageways 42 are provided in insertion tube 31 peripherally of central passageway 36 for carrying respective light fiber assemblies or light guides 43. A connection cable 46, a portion of which is shown in FIG. 1, extends from handle 33 to a conventional light source 47. First and send light guides 43 extend through insertion tube 31 and cable 46 for providing illumination forwardly of insertion tube 31.

A working passageway or channel 51 is further provided in insertion tube 31 and extends to a side port 52 formed in handle 33. An additional passageway 56 extends through insertion tube 31 and can be used as an air and/or water outlet. Insertion tube 31 is flexible so as to facilitate its insertion and advancement through a body and is provided with a bendable distal end for selectively directing distal face 32 in a desired direction. A plurality of finger operable controls 57 are provided on handle 33 for, among other things, operating the bendable distal end of insertion tube 31 and the supply and removal of fluids through the insertion tube 31.

Needle assembly 26 can be of any conventional type such as a modified sclerotherapy needle similar to the Bard® Flexitip™ needle manufactured by C.R. Bard, Inc. of Billerica, Md. Needle assembly 26 includes a needle member or needle 61 having a proximal end portion 61a and a distal end portion 61b and an optional sleeve member or sleeve 62 having a proximal end portion 62a and a distal end portion 62b. Sleeve 62 is made from any suitable material such as plastic and has a lumen extending longitudinally therethrough for receiving the needle 61. The sleeve 62 and the needle 61 are slidable relative to each other in a longitudinal direction. Needle 61 and sleeve 62 can be slidably disposed within working channel 51 and side port 62 of insertion tube 31 and each have a length so that when distal end portions 61b and 62b are extending from distal extremity 31b of the insertion tube 31 or otherwise in the vicinity of distal face 32, proximal end portions 61a and 62a are accessible at side port 52.

The hollow needle 61 has a passage 63 extending longitudinally therethrough from proximal end portion 61a to distal end portion 61b. The modified needle distal end portion 61b is made from any suitable material such as stainless steel and has a size ranging from 16 to 28 gauge and preferably ranging from 23 to 26 gauge. As shown most clearly in FIG. 3, the distal end portion 61b has a cylindrical wall 66 for forming internal passage 63 and also has a sharpened or beveled distal end 67 formed in part by a tapered end surface 68. At least one opening 71 is provided in distaled portion 61 and can include or consist of an opening 71a provided in tapered end surface 68. As an alternative to or in addition to opening 71a, at least one and as shown a plurality of openings 71 can be provided in cylindrical wall 66. A plurality of two openings 71b and two additional openings 71c are provided in wall 66. Openings 71b are diametrically disposed relative to each other so as to be 180° apart, and openings 71c are also diametrically disposed relative to each other but offset 90° from openings 71b. The openings 71c are spaced longitudinally behind the openings 71b. Openings 71b and 71c can be any suitable shape or size and are shown as being elongate or oblong in shape. It should appreciated that a needle distal end portion 61b having only openings 71b or openings 71c can be provided and be within the scope of the present invention. In one embodiment of needle 61, tapered surface 68 is closed and openings 71 provided only in cylindrical wall 66.

Figure 4:
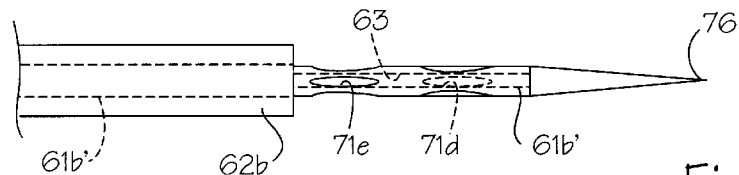
FIG. 4 is an enlarged side view, similar to FIG. 3, of the distal portion of another embodiment of the apparatus for use in the method for treating tracheo-esophageal fistulas of the present invention.

Another embodiment of the modified distal end portion of the needle 61 is shown in FIG. 4. Distal end portion 61b' therein has a sharpened or pointed distal end 76 which is generally conical in shape. No opening 71 is provided in the closed pointed end 76. A plurality of three circumferentially-disposed openings 71d are provided in cylindrical wall 66 proximal of pointed end 76. Openings 71d are circumferentially spaced apart at separation angles of approximately 120°. A second set of three openings 71e extend through cylindrical wall 66 proximal of openings 71d. Openings 71e are also circumferentially spaced apart at separation angles of approximately 120°. The openings 71e are angularly offset about the centerline of distal end portion 61b' relative to the opening 71d.

A fluid connector 81 is secured to proximal end portion 61a of needle 61 and a gripping member or grip 82 is secured to the proximal end portion 62a of the sleeve 62 (see FIG. 1). Fluid connector 81 includes first and second luer fitting portions 83 and 84, or any other suitable fitting portions, which communicate with passage 63 in needle 61. First luer fitting portion 83 is capped in FIG. 1. Fluid connector 81 and grip 82 are longitudinally movable relative to each other so as to cause relative longitudinal movement between needle 61 and sleeve 62. More specifically, grip 82 can be slid forwardly and rearwardly on proximal end portion 61a of the needle 61 relative to fluid connector 81. Movement of grip 82 forwardly relative to fluid connector 81 causes distal end portion 62b of sleeve 62 to extend fully over distal end portion 61b of the needle 61 so that the needle has fully retracted within sleeve 62. Conversely, movement of grip 82 rearwardly relative to fluid connector 81 causes sleeve distal end portion 62b to retract relative to needle distal end portion 61b so as to expose the needle distal end portion 61b.

The handle means of treatment device 21 includes supply assembly 27 coupled to proximal extremity 31a of insertion tube 31 (see FIG. 1). More specifically, supply assembly 27 is secured to the proximal extremity of needle assembly 26. The supply assembly 27 is included within the means of treatment device 21 for introducing a liquid or solution through passage 63 of needle 61 and out one or more of the openings 71 provided in the needle distal end portion 61b. Supply assembly 27 comprises a conventional syringe or first syringe 91 having a reservoir or barrel 92 provided with any suitable fitting portion such as luer fitting portion 93 at the forward end thereof and a plunger 94 for dispelling liquid within barrel 92 through luer fitting portion 93. The supply assembly 27 optionally includes second and third reservoir in the form of second and third syringes 96 and 97. The second syringe 96 is filled with dimethyl sulfoxide (DMSO) or any other suitable liquid. The third syringe 97 is filled with a saline solution or any other suitable aqueous or physiologic solution.

A manifold assembly or manifold 98 is provided for coupling syringes 91, 96 and 97 to fluid connector 81. In one embodiment, the manifold 98 has a plurality of three stop cocks 101–103 and a plurality of at least two and as shown a plurality of four ports or luer fitting portions. A first luer fitting portion 104 cooperatively mates with the forward luer fitting portion 93 of syringe 91. A second luer fitting portion 106 cooperatively mates with second luer fitting portion 84 of the fluid connector 81. Third and fourth luer fitting portions 107 and 108 are additionally provided. The third luer fitting portion 107 is connected by a tube 109, a portion of which is shown in FIG. 1, to second syringe 96 and the fourth luer fitting portion 108 is connected by a tube 110, a portion of which is shown in FIG. 1, to third syringe 97. The stop cocks 101–103 operate in a conventional manner to direct fluid flow between the luer fitting portions 104 and 106–108. In a further embodiment of the invention (not shown), syringe 91 can be secured directly to fluid connector 81 or the proximal end portion 61a of needle 61. It should be appreciated that manifold 98 can alternatively be provided with less than or greater than four luer fitting portions or be of any other configuration for coordinating fluid flow from a plurality of syringes or other fluid reservoirs.

Figure 5:
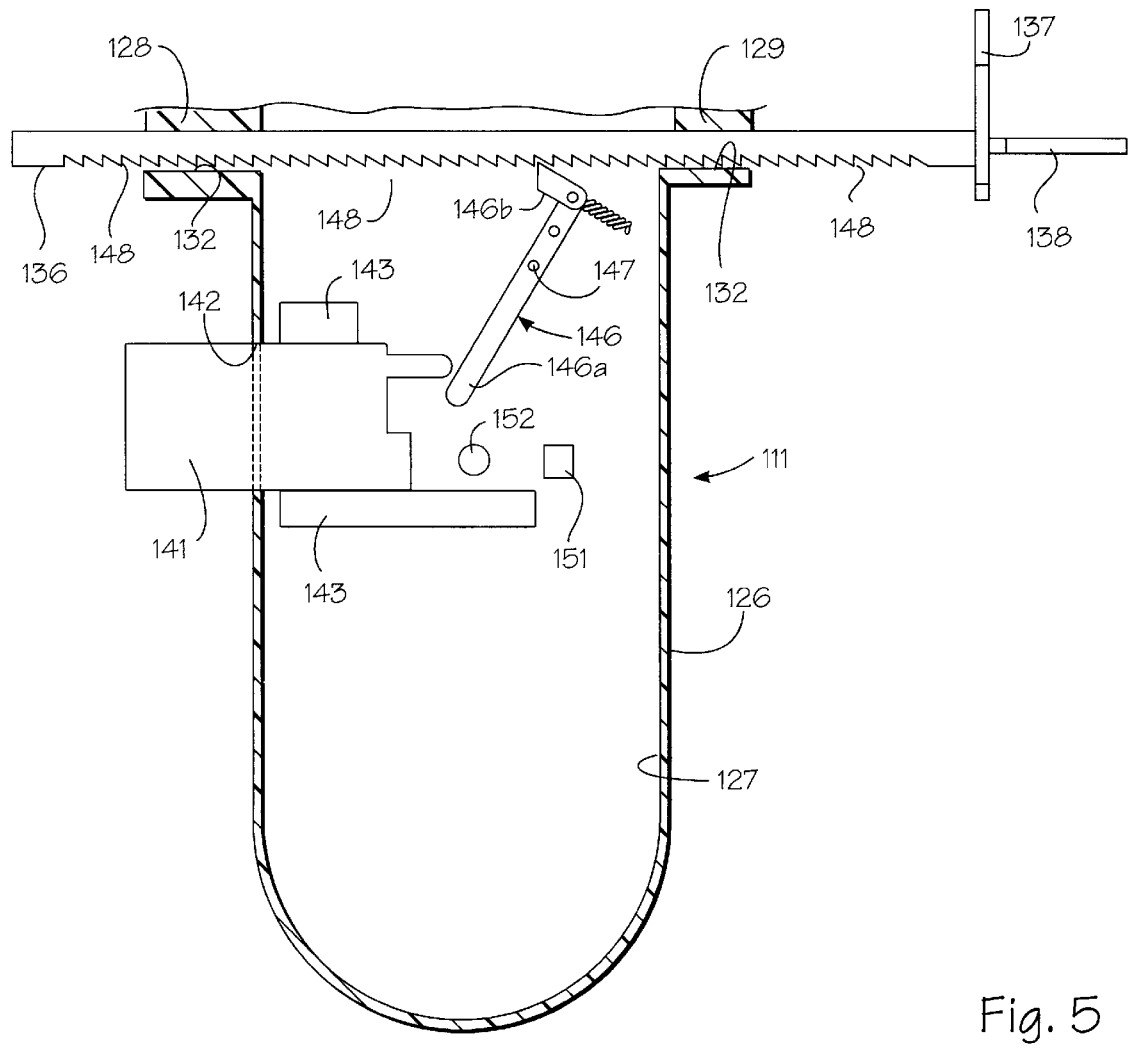
FIG. 5 is a cross-sectional view of a proximal portion of the apparatus of FIG. 1 taken along the line 5—5 of FIG. 1.

Supply assembly 27 further includes an optional delivery device or gun 111 for supplying a plurality of discrete preselected amounts of the fluid within barrel 92 to needle 61 (see FIGS. 1 and 5). Gun 111 has a cylindrical housing 112 made from plastic or any other suitable material for receiving syringe barrel 92. Housing 112 is formed from a base portion 113 and a cover portion 114 pivotally secured to the base portion 113 by hinge 116. A latch 117 is pivotally coupled to the cover portion 114 for engaging base portion 113 and thereby locking the cover portion 114 in a closed position. Housing 112 has a forward opening 118 for receiving luer fitting portion 93 of the syringe 91. A handle 126 made from plastic or any other suitable material depends from base portion 113. The handle 126 has an internal cavity 127. First and second spaced-apart reinforcing members 128 and 129 extend downwardly from the base portion 113 at the front and rear of handle 126. The reinforcing members 128 and 129 are longitudinally aligned and each provided with a bore 132 extending longitudinally therethrough and opening into internal cavity 127. A rod 136 made from plastic or any other suitable material is slidably disposed within bores 132. The rod 136 has a paddle 137 extending upwardly from the rear thereof perpendicularly to the longitudinal axis of the rod. Paddle 137 is adapted to engage the end of syringe plunger 94. A ring 138 sized for receiving a finger of a human hand extends rearwardly from paddle 137 for facilitating the pulling of rod 136 rearwardly in bores 132.

Rod 136 and paddle 137 are included within the finger operable means of gun 111 for causing incremental relative movement between barrel 92 and plunger 94 of the syringe 91. A trigger 141 extends from an opening 142 at the front of handle 126 below rod 136. The trigger is slidably disposed in a direction parallel to the longitudinal axis of rod 136 between first and second spaced-apart guides 143 provided in internal cavity 127. Trigger 141 moves between a first or fully extended position to a second or fully retracted position. A lever 146 is pivotally coupled to handle 126 by means of a pin 147. The lever 146 has a first end portion 146a which extends behind trigger 141 and a second end portion 146b having a wedge-like shape for engaging one of a plurality of longitudinally spaced-apart notches formed in the bottom of rod 136. When trigger 141 is pulled rearwardly by the finger of a human hand, the trigger engages lever first end portion 146a to cause the lever 146 to pivot about pin 147 from a first or home position to a second or operational position. Lever second end portion 146b moves forwardly during this half-stroke to engage one of notches 148 and cause the rod 136 to move forwardly relative to housing 112. The paddle 137 follows rod 136 and incrementally pushes plunger 94 into barrel 92 for each pull of trigger 141.

A fixed stop 151 is provided in handle 126 for limiting the rearward movement of trigger 141 and thus determining the incremental amount of fluid within barrel 92 dispelled from the syringe 91 with each pull of trigger 141. The rearward travel of trigger 141 can be selectively limited by means of one or more addition pins or stops 152, one of which is shown in FIG. 5. Adjustable limit pin 152 is slidably mounted within handle 126 for movement from a first position out of the path of trigger 141 to a second position within the path of the trigger 141 so as to selectively limit the rearward stroke of trigger 141 when engaged and placed in its second position.

A coil spring 156 or any other suitable biasing number having one end coupled to a pin 157 mounted within handle 126 and a second end secured to the second end portion 146b of lever 146 is provided. Spring 156 urges lever 146 back to its home position, out of engagement with notches 148, when the finger pressure on trigger 141 is released. Spring 156 causes lever first end portion 146a to push trigger 141 outwardly from opening 142 to its home position.

A finger operable adjustment mechanism 166 is connected to needle proximal end portion 61a and sleeve proximal end portion 62a for causing longitudinal relative movement between the needle 61 and the sleeve 62. The adjustment mechanism 166 can be of any suitable type for use with any suitable needle assembly having a needle and sleeve which are adjustable relative to each other. One embodiment of such an adjustment mechanism 166 is carried by gun 111. As shown in FIG. 1, such adjustment mechanism 166 has a first or forward post 167 and a second or rear post 168 extending upwardly from the top of cover portion 114. The longitudinally spaced-apart posts 167 and 168 extend perpendicularly to barrels 92. A slidable member or slide bar 171 is slidably mounted in a bore (not shown) provided in forward post 167 for forward and rearward movement in a direction parallel to barrel 92. A thumb screw 172 having an enlarged head 172a is slidably disposed in a bore (not shown) provided in rear post 168. Screw head 172a abuts rear post 168 and the other end of screw 172 is threadably received within the back end of slide bar 171. Counterclockwise rotation of thumb screw 172 relative to rear post 168 causes slide bar 171 to move rearwardly toward forward post 167, while clockwise rotation of the thumb screw 172 results in the slide bar 171 moving forwardly away from post 167. An L-shaped coupler 173 is pivotally coupled to the forward end of slide bar 171 by means of a pin 174. The coupler 173 has first and second spaced-apart arms 176 forming a slot 178 therebetween for receiving the central portion of grip 82. A screw 179 extends between the arms 176 for locking the arms to grip 82 and thus longitudinally locking sleeve 62 relative to needle 61.

Treatment device 21 can be used in the body of a mammal for any suitable procedure such as the treatment of the upper portion of the gastrointestinal tract. In one such procedure, device 21 is utilized for the treatment of a tracheo-esophageal fistula (see FIGS. 6–11). A portion of a human body 184 is shown in FIGS. 6–11 and has an internal cavity in the form of an intestinal tract 186 accessible from a natural body opening such as a mouth 187 and extending from the mouth to an anus (not shown). The intestinal tract 186 is formed by a wall 188 and includes an esophagus 191 extending from the mouth into a stomach (not shown). The esophageal mucosa 192 serves as the inner layer of the intraluminal wall 188 in the esophagus 191. Wall 188 further includes a layer of circular muscle 193 extending beneath mucosa layer 192 and a layer of longitudinal muscle 194 beneath circular muscle 193. The muscle layers 201 and 194 each extend around the esophagus 191. The wall 188 has a depth which includes at least mucosa layer 192, muscle layers 193 and 194 and any submucosal space created between mucosal layer 192 and circular muscle layer 193. A trachea 197 formed by a tubular wall 198 extends downwardly from the mouth 187 alongside esophagus 191 in the body 184. A trachea-esophageal fistula 201 extends through wall 188 of the esophagus 191 and wall 198 of the trachea 197 and creates an opening between the esophagus and the trachea.

In a method of the present invention, an inert, nonresorbable material is introduced into the body 184 to augment the wall of a hollow viscus in the body. More specifically, the material is introduced into wall 188 in the vicinity of fistula 201 so as to augment the wall 188. Although any suitable material can be used with the method and/or apparatus of the present invention, one such material comprises at least one solution which when introduced into the body forms a nonbiodegradable solid. As used herein, a solid means any substance that does not flow perceptibly under moderate stress, has a definite capacity for resisting forces which tend to deform it (such as compression, tension and strain) and under ordinary conditions retains a definite size and shape; such a solid includes, without limitation, spongy and/or porous substances. One such embodiment of the at least one solution is first and second solutions which when combined in the body form the nonbiodegradable solid. Another such embodiment is a nonaqueous solution which can be introduced into the body as a liquid and from which a solid thereafter precipitates. A preferred embodiment of such a nonaqueous or augmenting solution is a solutions of a biocompatible polymer and a biompatible solvent which can optionally include a contrast agent for facilitating visualization of the solution in the body.

A particularly preferred augmenting or bulking solution is a composition comprising from about 2.5 to about 8.0 weight percent of a biocompatible polymer, from about 52 to about 87.5 weight percent of a biocompatible solvent and optionally from about 10 to about 40 weight percent of a biocompatible contrast agent having a preferred average particle size of about 10 $\mu$m or less. It should appreciated that any percents stated herein which include a contrast agent would be proportionally adjusted when the contrast agent is not utilized. Any contrast agent is preferably a water insoluble biocompatible contrast agent. The weight percent of the polymer, contrast agent and biocompatible solvent is based on the total weight of the complete composition. In a preferred embodiment the water insoluble, biocompatible contrast agent is selected from the group consisting of barium sulfate, tantalum powder and tantalum oxide. In still a further preferred embodiment the biocompatible solvent is dimethylsulfoxide (DMSO), ethanol, ethyl lactate or acetone.

The term "biocompatible polymer" refers to polymers which, in the amounts employed, are non-toxic, chemically inert, and substantialy non-immunogenic when used internally in the patient and which are substantially insoluble in physiologic liquids. Suitable biocompatible polymers include, by way of example, cellulose acetates (including cellulose diacetate), ethylene vinyl alcohol copolymers, hydrogels (e.g., acrylics), poly($C_1$–$C_6$) acrylates acrylate copolymers, polyalkyl alkacrylates wherein the alkyl and alk groups independently contain one to six carbon atoms, polyacrylonitrile, polyvinylacetate, cellulose acetate butyrate, nitrocellulose, copolymers of urethane/carbonate, copolymer of styrene/maleic acid, and mixtures thereof. Copolymer of urethane/carbonate include polycarbonates that are diol terminated which are then reacted with a diisocyanate such as methylene bisphenyl diisocyanate to provide for the urethane/carbonate copolymers. Likewise, copolymers of styrene/maleic acid refer to copolymers having a ratio of styrene to maleic acid of from about 7:3 to about 3:7. Preferably, the biocompatable polymer is also non-inflammatory when employed in situ. The particular biocompatible polymer employed is not critical and is selected relative to the viscosity of the resulting polymer solution, the solubility of the biocompatible polymer in the biocompatible solvent, and the like. Such factors are well within the skill of the art.

The polymers of polyacrylonitrile, polyvinylacetate, poly($C_1$–$C_6$) acrylates, acrylate copolymers, polyalkyl alkacrylates wherein the alky and alk groups independently contain one to six carbon atoms, cellulose acetate butyrate, nitrocellulose, copolymers of urethane/carbonate, copolymers of styrene/maleic acid and mixtures thereof typically will have a molecular weight of at least about 50,000 and more preferably from about 75,000 to about 300,000.

Preferred biocompatible polymers include cellulose diacetate and ethylene vinyl alcohol copolymer. In one embodiment, the cellulose diacetate has an acetyl content of from about 31 to about 40 weight percent. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the implanting properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 8 weight-volume percent of the ethylene vinyl alcohol copolymer in DMSO has a viscosity equal to or less than 60 centipoise at 20° C. and more preferably 40 centipoise or less at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative water solubility insolubility of the composition as well as the rate of precipitation of the copolymer in an aqueous solution. In a particularly preferred embodiment, the copolymers employed herein comprise a mole percent of ethylene of from about 25 to about 60 and a mole percent of vinyl alcohol of from about 40 to about 75, more preferably a mole percent of ethylene of from about 40 to about 60 and a mole percent of vinyl alcohol of from about 40 to about 60.

The term "contrast agent" refers to a biocompatible (non-toxic) radiopaque material capable of being monitored during injection into a mammalian subject by, for example, radiography. The contrast agent can be either water soluble or water insoluble. Examples of water soluble contrast agents include metrizamide, iopamidol, iothalamate sodium, iodomide sodium, and meglumine. The term "water insoluble contrast agent" refers to contrast agents which are insoluble in water (i.e., has a water solubility of less than 0.01 milligrams per milliliter at 20° C.) and include tantalum, tantalum oxide and barium sulfate, each of which is commercially available in the proper form for in vivo use and preferably having a particle size of 10 μm or less. Other water insoluble contrast agents include gold, tungsten and platinum powders. Methods for preparing such water insoluble biocompatible contrast agents having an average particle size of about 10 μm or less are described below. Preferably, the contrast agent is water insoluble (i.e., has a water solubility of less than 0.01 mg/ml at 20° C.)

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, ethyl lactate, acetone, and the like. Aqueous mixtures with the biocompatible solvent can also be employed provided that the amount of water employed is sufficiently small that the dissolved polymer precipitates upon injection into a human body. Preferably, the biocompatible solvent is ethyl lactate or dimethylsulfoxide.

The term "encapsulation" as used relative to the contrast agent being encapsulated in the precipitate is not meant to infer any physical entrapment of the contrast agent within the precipitate much as a capsule encapsulates a medicament. Rather, this term is used to mean that an integral coherent precipitate forms which does not separate into individual components, for example into a copolymer component and a contrast agent component.

The compositions employed in the methods of this invention are prepared by conventional methods whereby each of the components is added and the resulting composition mixed together until the overall composition is substantially homogeneous. For example, sufficient amounts of the selected polymer are added to the biocompatable solvent to achieve the effective concentration for the complete composition. Preferably, the composition will comprise from about 2.5 to about 8.0 weight percent of the polymer based on the total weight of the composition and more preferably from about 4 to about 5.2 weight percent. If necessary, gentle heating and stirring can be used to effect dissolution of the polymer into the biocompatible solvent, e.g., 12 hours at 50° C.

Sufficient amounts of the contrast agent are then optionally added to the biocompatible solvent to achieve the effective concentration for the complete composition. Preferably, the composition will comprise from about 10 to about 40 weight percent of the contrast agent and more preferably from about 20 to about 40 weigh percent and even more preferably about 30 to about 35 weight percent. When the contrast agent is not soluble in the biocompatible solvent, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm). In one preferred embodiment, the appropriate particle size of the contrast agent is prepared, for example, by fractionation. In such an embodiment, a water insoluble contrast agent such as tantalum having an average particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatable solvent is not critical and stirring of the resulting suspension is conducted as necessary to achieve homogeneity of the composition. Preferably, mixing/stirring of the composition is conducted under an anhydrous atmosphere at ambient pressure. The resulting composition is heat sterilized and then stored preferably in sealed amber bottles or vials until needed.

Each of the polymers recited herein is commercially available but can also be prepared by methods well known in the art. For example, polymers are typically prepared by conventional techniques such as radical, thermal, UV, gamma irradiation, or electron beam induced polymerization employing, as necessary, a polymerization catalyst or polymerization initiator to provide for the polymer composition. The specific manner of polymerization is not critical and the polymerization techniques employed do not form a part of this invention. In order to maintain solubility in the biocompatible solvent, the polymers described herein are preferably not cross-linked.

In another particularly preferred embodiment of the augmenting solution the biocompatible polymer composition can be replaced with a biocompatible prepolymer composition containing a biocompatible prepolymer. In this embodiment, the composition comprises biocompatible prepolymer, an optional biocompatible water insoluble contrast agent preferably having an average particle size of about 10 μm or less and, optionally, a biocompatible solvent.

The term "biocompatible prepolymer" refers to materials which polymerize in situ to form a polymer and which, in the amounts employed, are non-toxic, chemically inert, and substantially non-immunogenic when used internally in the patient and which are substantially insoluble in physiologic liquids. Such a composition is introduced into the body as a mixture of reactive chemicals and thereafter forms a biocompatible polymer within the body. Suitable biocompatible prepolymers include, by way of example, cyanoacrylates, hydroxyethyl methacrylate, silicon prepolymers, and the like. The prepolymer can either be a monomer or a reactive oligomer. Preferably, the biocompatible prepolymer is also non-inflammatory when employed in situ.

Prepolymer compositions can be prepared by adding sufficient amounts of the optional contrast agent to the solution (e.g., liquid prepolymer) to achieve the effective concentration for the complete polymer composition. Preferably, the prepolymer composition will comprise from about 10 to about 40 weight percent of the contrast agent and more preferably from about 10 to about 40 weight percent and even more preferably about 30 weight percent. When the contrast agent is not soluble in the biocompatible prepolymer composition, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm).

When the prepolymer is liquid (as in the case of polyurethanes), the use of a biocompatible solvent is not absolutely necessary but may be preferred to provide for an appropriate viscosity in the augmenting solution. Preferably, when employed, the biocompatible solvent will comprise from about 10 to abut 50 weight percent of the biocompatible prepolymer composition based on the total weight of the prepolymer composition. When a biocompatible solvent is employed, the prepolymeric composition typically comprises from about 90 to about 50 weight percent of the prepolymer based on the total weight of the composition.

In a particularly preferred embodiment, the prepolymer is cyanoacrylate which is preferably employed in the absence of a biocompatible solvent. When so employed, the cyanoacrylate adhesive is selected to have a viscosity of from about 5 to about 20 centipoise at 20°C.

The particular order of addition of components is not critical and stirring of the resulting suspension is conducted as necessary to achieve homogeneity of the composition. Preferably, mixing/stirring of the composition is conducted under an anhydrous atmosphere at ambient pressure. The resulting composition is sterilize and then stored preferably in sealed amber bottles or vials until needed.

Specific embodiments of augmenting solutions suitable for use in the apparatus and methods of the invention are described in U.S. Pat. No. 5,667,767 dated Sep. 16, 1997, U.S Pat. No. 5,580,568 dated Dec. 3, 1996 and U.S Pat. No. 5,695,480 dated Dec. 9, 1997 and International Publication Number WO 97/45131 having an International Publication Date of Dec. 4, 1997, the entire contents of which are incorporated herein by this reference.

In operation and use of treatment device 21 in the method of the present invention, syringe 91 is filled with the augmenting solution in preparation of the procedure. The syringe 91 is loaded into gun 111 by opening cover portion 114 to permit placement of barrel 92 within housing 112. Ring 138 is grasped to pull rod 136 rearwardly relative to housing 112 so that paddle 137 is disposed behind the retracted plunger 94. Cover portion 114 is closed and secured to base portion 113 by means of latch 117. The physician thereafter pulls trigger 141 as necessary to cause paddle 137 to engage the rear of plunger 94.

Although the method of the present invention permits supply assembly 27 to be attached to needle assembly 26 after needle 61 and sleeve 62 have been disposed in working channel 51 of probe 22, the method alternatively permits the supply assembly 26 to be attached to the needle assembly prior to such disposition of the needle assembly within probe 22. In either case, attachment is accomplished by coupling first luer fitting portion 104 of manifold 98 to luer fitting portion 93 of syringe 91 and second luer fitting portion 106 of the manifold to the first luer fitting portion 83 of fluid connector 81. Coupler 173 is pivoted downwardly so that first and second arms 176 thereof engage grip 82 and screw 179 tightened to secure the grip 82 in the slot 178 between arms 176. Thumb screw 172 is rotated in a counterclockwise direction relative to rear post 191 to ensure that needle 61 is fully retracted within sleeve 62. Thereafter, saline solution syringe 97 is coupled by means of tube 110 to third luer fitting portion 107 of the manifold 98 and DMSO syringe 96 is coupled by means of tube 109 to fourth luer fitting portion 108 of the manifold.

Probe 22 is prepared by connecting light cable 46 to light source 47 and attaching the proper eyepiece 41 to handle 33. In addition, all other conventional attachments are applied to the probe 22.

After the patient has been appropriately sedated or anesthetized, probe distal extremity 31b is introduced through mouth 187 into esophagus 191. In this regard, probe handle 33 is grasped by the physician to introduce distal extremity 31b of probe 22 into mouth 187 and advance the insertion tube 31 down esophagus 191 to the vicinity of the fistula 201. Optical viewing device 23 facilities such advancement by the physician of insertion tube 31. Insertion tube 31 has a length so that when distal extremity 31b is in the vicinity of the fistula 201, proximal extremity 31a is outside of body 184.

Distal end portion 61b and 62b of needle assembly 26 are now inserted through side port 52 of insertion tube 31 and advanced until such distal end portions of needle 61 and sleeve 62 are in the vicinity of insertion tube distal extremity 31b. Needle 61 and sleeve 62 are each movable from a first position in which distal end portions 61b and 62b are each retracted within insertion tube 31 and thus recessed within working channel 51 to a second position in which the distal end portions 61b and 62b extend distally beyond the end of insertion tube 31. The needle and sleeve each have a sufficient length so that the physician holding gun 111 can extend both the needle and the sleeve distally from distal extremity 31b a significant distance, should that be desired.

Figure 6:
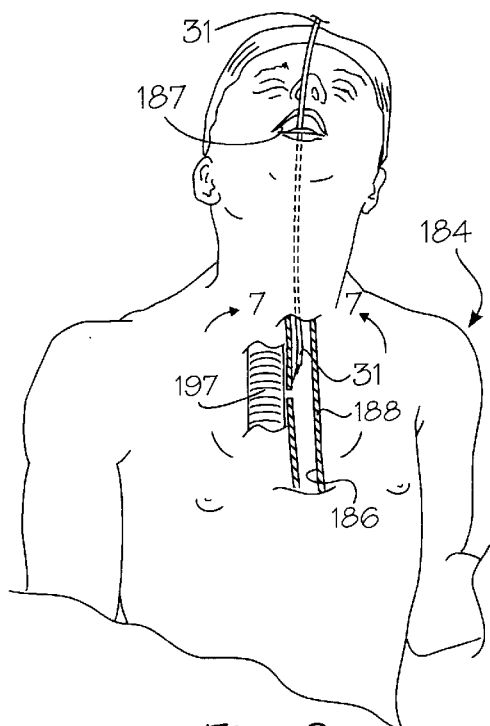
FIG. 6 is a schematic view of the apparatus of FIG. 1 practicing the method for treating tracheo-esophageal fistulas of the present invention.
Figure 7:
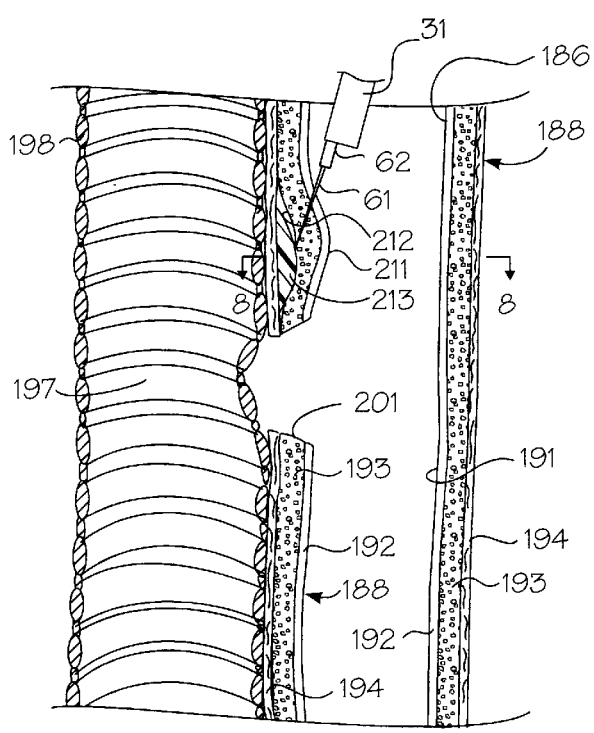
FIG. 7 is an enlarged sectional view of a portion of the esophagus and trachea of FIG. 6 taken along the line 7—7 of FIG. 6.
Figure 8:
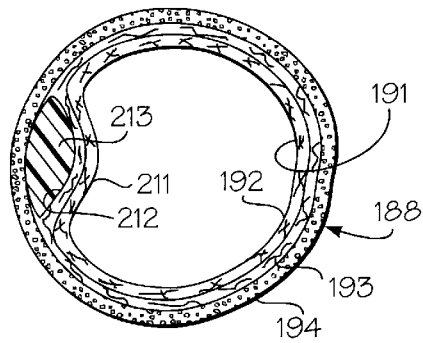
FIG. 8 is a cross-sectional view of the esophagus of FIG. 7 taken along the line 8—8 of FIG. 7 showing a portion of the esophagus as augmented by the method of the present invention.

A portion of the procedure for augmenting wall 188 in the vicinity of a fistula 201 is shown in FIGS. 6 and 7. Under the guidance of optical viewing device 23, insertion tube distal extremity 31b is maneuvered to a position above the portion of wall 188 which is to be augmented. The physician retracts sleeve 62 relative to needle 61 by means of adjustment mechanism 166 so that needle distal end portion 61b extends beyond sleeve distal end portion 62b a selected amount of at least 2 millimeters and preferably ranging from 2 to 15 millimeters. Such amount of extension can be easily determined for example by correlating such extension as a function of the rotation of thumb screw 172 and properly calibrating the position of thumb screw 172 relative to rear post 168 in this regard. The retraction of needle 61 relative to sleeve 62 can occur either within working channel 51 or after the needle 61 and sleeve 62 have been extended from insertion tube distal extremity 31b. The physician primes needle 61 with the saline or other aqueous or physiologic solution from syringe 97 and ensures that needle passage 63 is filled with saline solution by observing with optical viewing device 23 the saline solution being dispelled from one or more openings 71 in needle distal end portion 61b. For simplicity, the operation of conventional stop cocks 101–103 for directing appropriate fluids to and from needle passage 63 will not be discussed in connection with the procedure.

The physician causes sharpened end 67 of needle 61 to penetrate wall 188 by moving the needle 61 and sleeve 62 closer to side port 52. The field of view of optical viewing device 23 permits the physician to observe the penetration of wall 188. Although the needle 61 and sleeve 62 can penetrate the wall 188 at any angle, it is preferred that the angle of penetration relative to wall 188 be less than 90° and more preferably less than 40°. In the injection shown in FIG. 7, the saline solution is being introduced into wall 188 above the fistula 201 and preferably below the cricopharyngeus muscle. Saline solution is injected into wall 188 and more specifically into one of muscle layers 193 or 194 or between the layers 193 and 194. The saline injection creates an enlargement 211 in wall 188 having an internal space 212 filled with the saline solution. The amount of saline solution required to create space 222 can range from 0.25 to 10 cc and preferably range from 1 to 3 cc.

After the creation of enlargement 211, the physician retracts needle 61 from space 212 and withdraws the remaining saline solution from passage 63 by means of pulling back the plunger on syringe 97 or by any other suitable method. The physician next cleanses needle passage 63 with DMSO from syringe 96 to ensure that the saline solution has been removed from passage 63. DMSO cleansing can be determined by observing a slight amount of DMSO being dispelled from needle distal end portion 61b. This cleansing step is enhanced by the introduction of the DMSO downstream of saline stop cock 103 and upstream of augmenting solution stop cock 101. The INSO is now removed from passage 63 by withdrawing the plunger of syringe 96 or by any other suitable means. Removal of the saline solution from passage 63 and the cleansing of the passage with DMSO inhibits premature precipitation within syringe 91 of the biocompatible polymer in the augmenting solution from the DMSO it the augmenting solution. Needle passage 63 is next primed with the augmenting solution carried by syringe 91 until such solution is available at the openings 71 in needle distal end portion 61b.

The physician positions insertion tube distal extremity 31b in the esophagus and causes needle distal end portion 61b to penetrate the enlargements 211 and extend into the saline filled space 212. Thereafter, the physician pulls trigger 141 to cause the desired preselected amount of augmenting solution to be introduced through needle 61 extending through probe 22. The openings 71 in needle distal end portion 61b are positioned so that the augmenting solution is preferably introduced into the middle of space 212. The optional contrast agent within the augmenting solution permits the viewing of the augmenting solution by means of fluoroscopy. In addition, the introduction of the augmenting solution into wall 188 can be monitored transabdominally or transesophageally by ultrasound. The rate of injection of the augmenting solution into space 212 can range from 0.1 cc per minute to 10 cc per minute.

Once the augmenting solution has been introduced into wall 188, the biocompatible polymer of the augmenting solution precipitates to form one or more discrete deposits or solid implants 213 (see FIG. 7). The amount of augmenting solution injected into wall 188 for each implant can range from 0.05 cc to 10 cc. The ratio of augmenting solution to saline in space 212 can range from 2:1 to 1:8 and preferably range from approximately one part augmenting solution to two to three parts saline solution. In one embodiment, the space 212 created by the saline solution predefines the configuration of the precipitant or implant 213. As can be seen from FIG. 7, the discrete implant 213 shown therein occupies less than all of space 212. In another embodiment (not shown), more augmenting solution than saline is introduced into the wall 188 so that the discrete implant 213 more than fills the space 212 created by the saline. After completion of the injection of augmenting solution and the solidification of the biocompatible polymer, the remaining solution within space 212 disperses within body 184 and the space 212 contracts about implant 213 (see FIG. 8).

Figure 9:
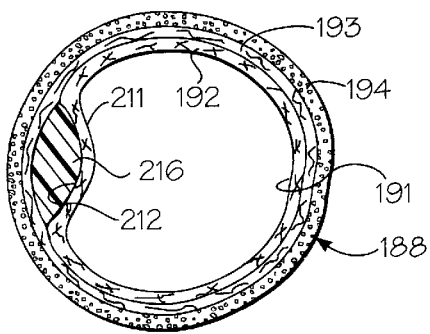
FIG. 9 is a cross-sectional view, similar to FIG. 8, of a portion of the esophagus as augmented by the method of the present invention.
Figure 10:
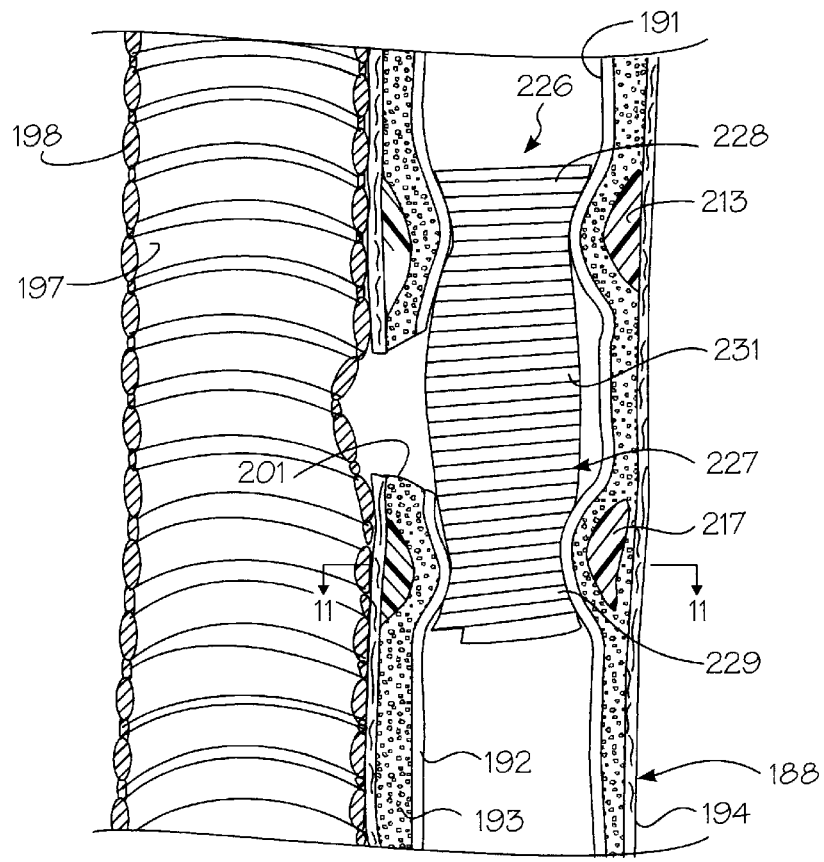
FIG. 10 is an enlarged sectional view, similar to FIG. 7, of a portion of the esophagus and trachea as treated by the method of the present invention.

In a further method of the present invention, an implant can be formed in portions of the wall 188 other than muscle layers 193 and/or 194 to bulk the wall 188 in the vicinity of fistula 201. For example, as shown in FIG. 9, an implants 216 can be formed beneath mucosa layer 192.

Although only a single implant can be created in wall 188 in the method of the present invention, a plurality of implants 213 are created in wall 188 in one preferred method of the invention. In preparation thereof, needle 61 is removed from enlargement 211 and the augmenting solution within passage 63 withdrawn by pulling back on plunger 94. The needle 61 is cleansed with DMSO by filling the needle passage 63 with DMSO from syringe 96 and thereafter withdrawing the DMSO from the passage 63. After the subsequent priming needle passage 63 with saline solution from syringe 97, the procedure discussed above can be repeated to create such additional implants 213.

Figure 11:
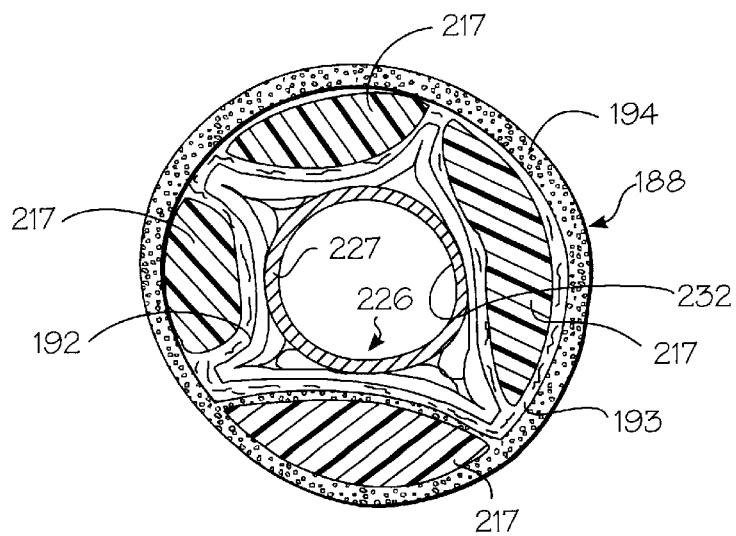
FIG. 11 is a cross-sectional view of the esophagus of FIG. 10 taken along the line 11—11 of FIG. 10.

The number and configuration of implants 213 formed in wall 188 can vary. In one preferred method of the invention, a plurality of implants 213 are created in wall 188 above fistula 201 and a second plurality of implants 217 are created in the wall 188 below the fistula (see FIGS. 10 and 11). Implants 213 and 217 are each somewhat pillow-like in shape and are preferably circumferentially spaced-apart around the periphery of the esophagus. More specifically, first or upper implants 213 are disposed substantially in a first plane extending perpendicularly to a longitudinal axis extending along the centerline of esophagus 191 and second or lower implants 217 are disposed substantially in a second plane extending perpendicularly to such longitudinal axis. An exemplary rosette of four implants 217 spaced-apart around the center of the rosette at approximately 90° intervals is shown in FIG. 11. It should be appreciated, however, that less than four or greater than four implants 213 and that less than four or greater than four implants 217 can be provided and formed in wall 188 and can be circumferentially spaced-apart at approximately equal angular intervals or asymmetrically disposed about the center line of esophagus 191. Implants which merge with adjacent inplants in wall 188 are within the scope of the present invention. Implants 213 can be longitudinally aligned or otherwise configured with respect to implants 217. In other methods of the invention, implants can be formed which are not disposed in a single plane. It is preferable that the sizing, spacing and configuration of implants 213 and implants 217 each be such so as to partially but not completely coapt the esophagus.

Although the method of the invention has been described as including the formation of a space 212 by a saline solution injected into the wall 188 prior to an injection of augmenting solution into the wall 188, it should be appreciated that space 212 can ba formed by other aqueous or physiologic solutions or by a local anesthetic. Alternatively, the augmenting solution can be injected into wall 188 without the prior formation of a space 212 by an injection of saline solution or otherwise. A saline or other aqueous or physiologic solution can optionally be introduced into such a space formed by the augmenting solution, that is after the introduction of the augmenting solution into the wall 188, to facilitate dispersion of the DMSO or other biocompatible solvent present in the augmenting solution. It should be further appreciated that the invention is broad enough to cover the introduction of an augmenting solution into wall 188 without the prior or subsequent introduction of a saline or other aqueous solution into the wall 188. In an alternative method for forming a plurality of implants within wall 188, a plurality of spaces 212 can be formed by saline solution from syringe 97. Subsequently, the augmenting solution from syringe 91 can be sequentially injected into each of such spaces.

In a further step of the method of the invention, a suitable stent 226 such as the EsophaCoil™ Self-expanding esophageal stent made by Instent of Eden Prairie, Minnesota is introduced into the esophagus in a conventional manner. Stent 226 is formed from a tubular body 227 that extends along a longitudinal axis. Body 227 has first and second end portions 228 and 229 and a central portion 231 located between the end portions 228 and 229. A passageway 232 extends longitudinally through body 227 between the end portions 228 and 229. The tubular body 227 has a relatively constant thickness along its length and is flaired at each of first and second enlarged end portions 228 and 229. In this regard, the first or proximal end portion 228 and second or distal end portion 229 each have a frusto-conical or funnel-like shape with inner and outer diameters that increase in a substantially linear manner from central portion 231 toward the first and second ends of body 227. The coiled body 227 of stent 226 is made from any suitable material such as Nitinol.

Stent 226 is placed in esophagus 191 so as to extend over fistula 201 and serve as a conduit for material traveling down the esophagus. It is preferable that the "funnel rim" of stent first end portion 228 be disposed at least two centimeters distal to the cricopharyngeus muscle. Body 227 has a length at least equal to the diameter or size of the fistula 201 and more preferably has a length greater than the diameter or size of the fistula. More specifically, stent 226 is longitudinally sized so that first and second flaired end portions 228 and 229 extend over and rest upon respective first and second sets of implants 213 and 217 (see FIG. 10).

Implants 213 and 217 created by the method and apparatus of the invention add bulk to the wall 188 so as to create a mechanical support for retaining stent 226 within its desired location within esophagus 191. In this regard, first and second implants 213 and 217 engage the frusto-conically shaped end portions 228 and 229 of body 227 so as to longitudinally secure stent 226 within esophagus 191 in a position extending over fistula 201. In a preferable procedure, implants 213 and 217 are sized so as to snugly engage the outside of stent 226 and thus substantially seal the fistula 201 from the contents of the esophagus 191. In this manner, the method of the invention serves to enhance the isolation of fistula 201 and thus minimize material traveling within the esophagus from undesirably accessing the trachea. Among other things, aspiration of gastric contents and saliva and the passage of digested food into the bronchopulmonary tree are minimized. The method of the invention also serves to relieve dysphagia.

It should be appreciated that some or all of implants 213 and/or 217 can be formed in wall 188 after stent 226 has been positioned within esophagus 191. For example, lower implants 217 can be formed in the wall 188 below fistula 201 before introduction of stent 226 into the esophagus 191. After stent placement, upper implants 213 can be formed in the wall 188 by means of needle 61 or otherwise to further secure stent 226 within the esophagus.

Figure 12:
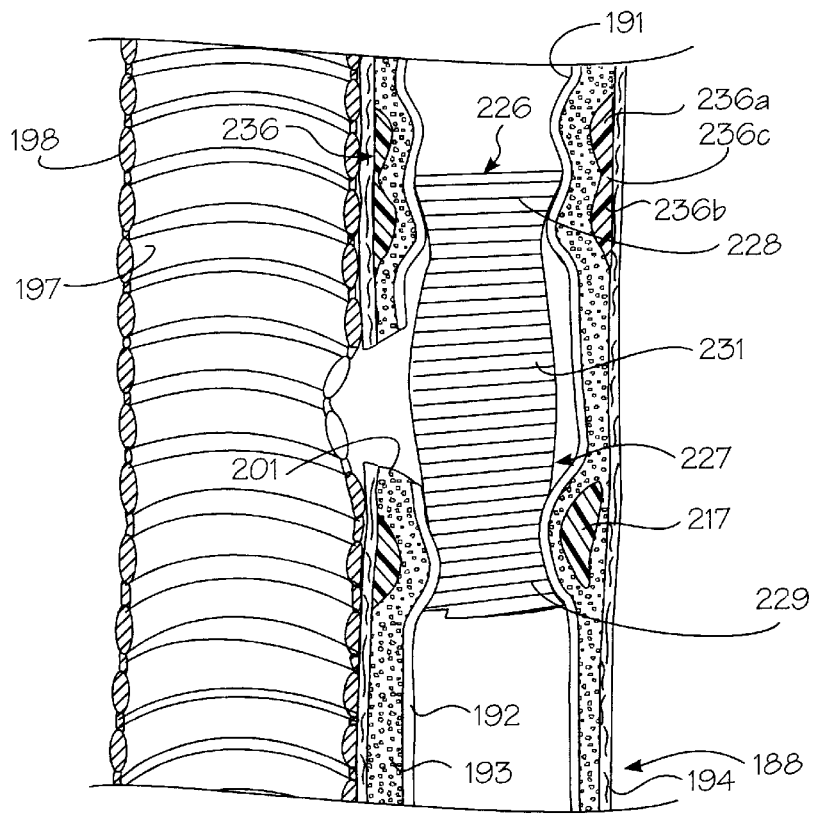

In another method of the invention, one or more implants are formed in wall 188 above first end portion 228 of stent 226 and/or below second end portion 229 of the stent. In one such exemplary method, a plurality of first or proximal implants 236 are formed in wall 188 in the vicinity of upper or proximal end portion 228 of the stent (see FIG. 12). The implants 236 are formed substantially in a plane extending perpendicularly to the centerline of esophagus 191 and can be symmetrically or asymmetrically arranged around such centerline in any of the configurations discussed above. Each of implants 236 has a first or upper portion 236a disposed above stent proximal end portion 228 and a second or lower portion 236b disposed below the upper end of stent 226. The enlarged upper and lower portions 236a and 236b are joined by a narrow central portion 236c. Proximal or upper implants 236 can be formed in wall 188 either before or after placement of stent 226 in esophagus 191. When the implants 236 are formed before stent placement, each of implants 236 can be formed so as to have a pillow-like shape which, when engaged by stent proximal end portion 227, transforms into an implant having a narrow central portion 236c and enlarged upper and lower end portions 236a and 236b.

A plurality of lower or distal implants substantially similar in shape to proximal implants 236 can be formed in the vicinity of stent distal end portion 229 in place of or in addition to implants 217. Each of such implants, not shown, can have an enlarged upper portion disposed in wall 188 above the distal end of stent 226, an enlarged lower portion below stent distal end portion 229 and a narrow central portion between the upper and lower portions.

Figure 13:
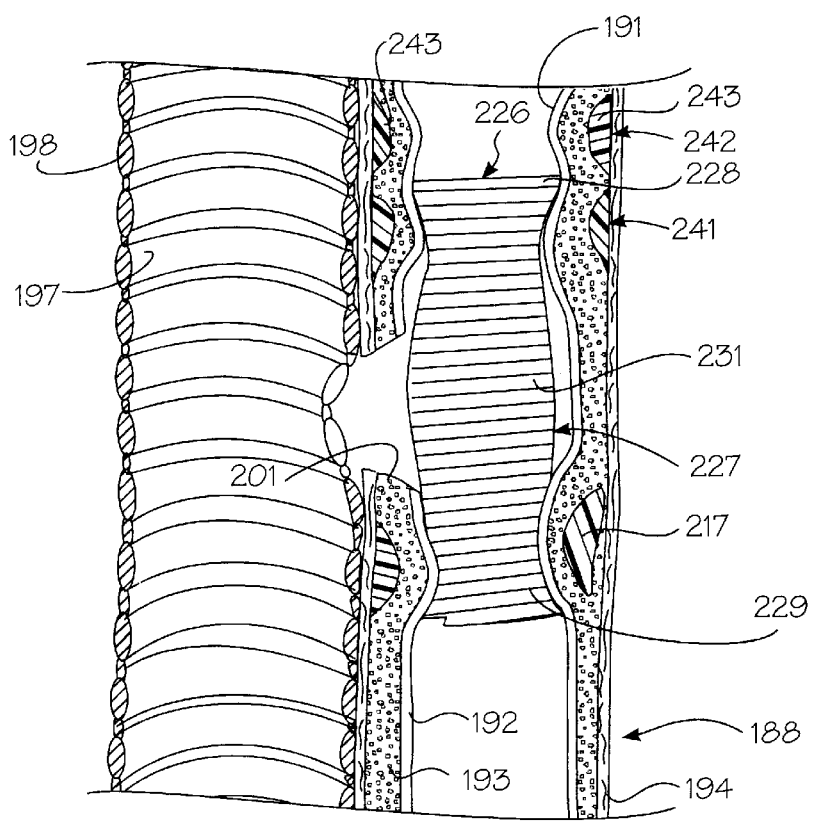

In a further method of the invention, first and second sets 241 and 242 of implants are formed in wall 188 in the vicinity of stent proximal end portion 228 (see FIG. 13). The first set 241 of implants consists of a plurality of implants 213 disposed below the proximal end of stent 226. The second set 242 of implants consists of a plurality of implants 243 disposed above proximal end portion 228 of the stent 226. Implants 213 and 243 are each disposed substantially in a plane extending perpendicularly to the centerline of esophagus 191. The implants 213 and 243 are longitudinally spaced apart so that the enlarged proximal end of stent 226 seats between the implants 213 and 243. In this manner, stent 226 is longitudinally fixed within the esophagus 191. Implants 213 and 243 can be formed either before or after placement of stent 226 in the esophagus 191. Second implants 217 can be optionally provided.

In further methods of the invention (not shown), only a single set of implants are formed in wall 188 in the vicinity of fistula 201 for securing stent 226 within esophagus 191. Such implants, preferably disposed substantially in a plane extending perpendicularly to the center line of the esophagus 191, can be formed in the vicinity of stent proximal end portion 228 or stent distal end portion 229 or elsewhere. When so formed in the vicinity of stent proximal end portion 228, such implants can be similar to implants 213, 236 or 243. When such implants are formed in the vicinity of stent distal end portion 229, implants substantially similar to implants 217 can be utilized. Alternatively, a plurality of implants (not shown) can be formed in a plane disposed below the distal end of stent 226 either in place of or in combination with implants 217. In a further alternative and as discussed above, a plurality of implants substantially similar to implants 236 can be formed in wall 188 in the vicinity of stent distal end portion 229.

It should be appreciated from the foregoing that one or more implants in a variety of configurations can be formed in wall 188 for retaining stent 226 within esophagus 191 so as to isolate fistula 201.

It should be appreciated that the implants of the present invention ran be used as delivery vehicles for other materials such as radio isotopes, chemotherapeutic agents, anti-inflammatory agents and or antibiotics. In addition, treatment device 21 can be used for introducing other materials, such as suspensions and the contrast agent, into a body and more specifically into a wall such as wall 188 in the body.

The optional contrast agent in the implants permits the implants to be monitored after completion of the procedure described above. Thus the stability of the implant and its configuration can be observed over time. Further procedures can be performed to supplement previously formed implants.

The needle assembly of the present invention can have other configurations. For example, needle 61 can be provided with a plurality of lumens or passages extending longitudinally therethrough for permitting multiple liquids to be separately carried by the needle. In a further alternative embodiment, a plurality of needles can be introduced through the working channels of any suitable probe such as probe 22. Each of such needles can be used to perform one or more of the steps of the invention. For example, separate needles can be provided for the introduction of the saline solution or other physiologic or aqueous solution, for the introduction of the DMSO or other biocompatible solvent and for the introduction of the augmenting solution.

Other supply assemblies, such as any of those described in copending U.S. patent application Ser. No. 09/232,056 filed Jan. 15 1999, can be used with probe 22 and needle assembly 26 in the method of the invention. In addition, although the method and apparatus of the invention have been described as utilizing a biocompatible polymer and a biocompatible solvent, the method and apparatus can be modified as necessary when other solutions such as those containing prepolymers are utilized. It should be appreciated that the syringes or other reservoirs described herein can be manually operated, as shown, or automated. For example, a conventional single-speed, multi-speed, programmable or other syringe pump can be used for automation. Further, in procedures where no saline or similar solution is utilized, the saline solution syringe and the related saline solution fluid flow hardware need not be provided in the treatment device. The method of the invention is not limited to the transesophageal or intraesophageal method described above. The augmenting method herein can also be performed by surgical procedures such as a laparotomy thoracotomy, laparoscopy or thoracoscopy. The method of the invention can be utilized for treating fistulas in the trachea or other lumens in the body of a mammal.

Other suitable materials can be utilized for augmenting or bulking the esophageal wall for facilitating the support of a stent in the esophagus. Such materials include injectable bioglass as described in Walker et al., "Injectable Bioglass as a Potential Substitute for Injectable Polytetrafluorethylene Particles", J.Urol., 148:645-7, 1992, small particle species such as polytetrafluoroethylene (PTFE) particles in glycerine such as Polytef®, biocompatible compositions comprising discrete, polymeric and silicone rubber bodies such as described in U.S. Pat. Nos. 5,007,940, 5,158,573 and 5,116,387 to Berg, biocompatible compositions comprising carbon coated beads such as disclosed in U.S. Pat. No. 5,451,406 to Lawin, collagen and other biodegradable material of the type disclosed in U.S. Pat. No. 4,803,075 to Wallace et al. and other known injectable materials.

From the foregoing, it can be seen that a minimally invasive method for treating tracheo-esophageal fistulas has been provided. In one preferred procedure, one or more implants are formed in the wall of the esophagus for facilitating support of a stent in the esophagus and formation of a seal between the esophageal wall and the stent. A suitable material such as a nonbiodegradable material can be injected into the wall of the esophagus for forming the one or more implants and augmenting the wall. The nonbiodegigadable material is injected as at least one solution and thereafter forms a solid. The at least one solution includes a solution from which a nonbiodegradable solid precipitates. The solution can include a biocompatible polymer and a biocompatible solvent. In a particularly preferred procedure, a first plurality of implants is formed in the wall above the fistula and a second plurality of implants is formed in the wall below the fistula. A stent is placed in the esophagus to isolate the fistula.

What is claimed is:

1. A method for treating a tracheo-esophageal fistula in a body of a mammal having a trachea and an esophagus each extending from a mouth wherein the fistula extends through a wall forming the esophagus into the trachea comprising the steps of augmenting the wall in the vicinity of the fistula and placing a stent over the fistula in the esophagus so as to inhibit material traveling down the esophagus from passing into the trachea, the augmenting of the wall facilitating support of the stent in the esophagus so as to enhance isolation of the fistula.

2. The method of claim 1 wherein the augmenting step includes the step of introducing at least one nonaqueous solution into the wall in the vicinity of the fistula and forming from the at least one nonaqueous solution a nonbiodegradable solid in the wall.

3. The method of claim 2 wherein the at least one solution is a solution of a biocompatible polymer and a biocompatible solvent an wherein the forming step includes the step of precipitatig the biocompatible polymer from the solution so that the biocompatible polymer solidifies in the wall so as to augment the wall and the biocompatible solvent disperses in the body.

4. The method of claim 3 wherein the solution of the biocompatible polymer and the biocompatible solvent has a composition comprising from about 2.5 to about 8.0 weight percent of a biocompatible polymer, from about 10 to about 40 weight percent of water insoluble biocompatible contrast agent and from about 52 to about 87.5 weight percent of a biocompatible solvent.

5. The method of claim 3 wherein the solution of the biocompatible polymer and the biocompatible solvent has a composition comprising from about 2.5 to about 8.0 weight percent of a biocompatible polymer, from about 10 to about 40 weight percent of a water soluble biocompatible contrast agent and from about 52 to about 87.5 weight percent of a biocompatible solvent.

6. The method of claim 3 wherein the introducing step includes the steps of extending a needle into the wall and supplying the biocompatible polymer and the biocompatible solvent through the needle into the wall.

7. The method of claim 2 wherein the forming step includes the step of forming a plurality of discrete nonbiodegradable solids in the wall.

8. The method of claim 2 wherein the forming step includes the step of forming a plurality of discrete nonbiodegradable solids in the wall disposed substantially in a plane extending perpendicularly to a centerline of the esophagus.

9. The method of claim 8 wherein the plane is disposed above the fistula.

10. The method of claim 8 wherein the plane is disposed below the fistula.

11. The method of claim 10 further comprising the step of forming a plurality of discrete nonbiodegradable solids in the wall disposed substantially in an additional plane extending perpendicularly to the centerline, the additional plane being disposed above the fistula.

12. The method of claim 8 wherein the plurality of discrete nonbiodegradable solids are disposed around the periphery of the esophagus.

13. The method of claim 1 wherein the mammal is a human.

14. The method of claim 1 wherein the placing step includes the step of placing a stent having first and second enlarged end portions in the esophagus, the first and second enlarged end portions facilitating retention of the stent in the esophagus.

15. A method for treating a tracheo-esophageal fistula in a body of a mammal having a trachea and an esophagus each extending from a mouth wherein the fistula extends through a wall forming the esophagus into the trachea comprising the steps of forming at least one implant in the wall in the vicinity of the fistula so as to add bulk to the wall and placing a stent over the fistula in the esophagus so as to inhibit material traveling down the esophagus from passing into the trachea, the bulking of the wall facilitating support of the stent in the esophagus and thereby enhancing isolation of the fistula.

16. The method of claim 15 wherein the forming step includes the step of forming at least one nonbiodegradable implant in the wall.

17. The method of claim 15 wherein the forming step includes the step of introducing at least one nonaqueous solution into the wall.

18. The method of claim 15 wherein the placing step includes the step of placing the stent over the implant.

19. A method for treating a tracheo-esophageal fistula in a body of a mammal having a trachea and an esophagus each extending from a mouth wherein the fistula extends through a wall forming the esophagus into the trachea comprising the steps of forming at least one nonbiodegradable implant in the wall in the vicinity of the fistula so as to add bulk to the wall and placing a stent in the esophagus over the at least one implant and the fistula so as to inhibit material traveling down the esophagus from passing into the trachea, the bulking of the wall facilitating support of the stent in the esophagus and thereby enhancing isolation of the fistula.

20. The method of claim 19 wherein the at least one implant is a nonbiodegradable insert.

* * * * *